US012594394B2

(12) United States Patent
Whittaker et al.

(10) Patent No.: US 12,594,394 B2
(45) Date of Patent: Apr. 7, 2026

(54) ARRANGEMENTS FOR HEADGEAR STRAP MANAGEMENT

(71) Applicant: KONINKLIJKE PHILIPS N.V., Eindhoven (NL)

(72) Inventors: Melody Anne Whittaker, Pittsburgh, PA (US); Joyce van Zanten, Eindhoven (NL); Nicolaas Petrus Willard, Eindhoven (NL); Marco Baragona, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 946 days.

(21) Appl. No.: 17/846,206

(22) Filed: Jun. 22, 2022

(65) Prior Publication Data

US 2023/0001124 A1     Jan. 5, 2023

Related U.S. Application Data

(60) Provisional application No. 63/216,825, filed on Jun. 30, 2021.

(51) Int. Cl.
 *A61M 16/06*          (2006.01)
 *A61M 16/08*          (2006.01)
(52) U.S. Cl.
 CPC .... *A61M 16/0683* (2013.01); *A61M 16/0875* (2013.01)
(58) Field of Classification Search
 None
 See application file for complete search history.

(56) References Cited

U.S. PATENT DOCUMENTS

| | | | | |
|---|---|---|---|---|
| 2,928,387 A | * | 3/1960 | Layne | A62B 18/084 128/201.19 |
| 6,588,424 B2 | * | 7/2003 | Bardel | A62B 18/084 128/207.11 |
| 8,074,651 B2 | * | 12/2011 | Bierman | A61M 16/0683 128/206.27 |
| 2009/0032026 A1 | * | 2/2009 | Price | A61M 16/06 128/207.11 |
| 2013/0228173 A1 | * | 9/2013 | Busch | A61M 16/0633 128/202.27 |

(Continued)

FOREIGN PATENT DOCUMENTS

WO          2020261138 A1    12/2020

*Primary Examiner* — Bradley H Philips
(74) *Attorney, Agent, or Firm* — Michael W. Haas

(57) ABSTRACT

A headgear for securing a patient interface to a patient's head includes a rear member and a pair of lower strap members. Each lower strap member is sized and configured to be positioned on a respective side of the head of the patient when the headgear arrangement is disposed on the head of the patient. Each lower strap member includes a free end that is selectively directly coupleable to the patient interface. The arrangement also includes a pair of strap management arrangements, with each arrangement positioned on a respective side of the headgear and structured to locate/hold the free end of a lower strap member of the pair of lower strap members in a predetermined location on the respective side of the head of the patient when the headgear is positioned on the head of the patient and the free end is not directly coupled to the patient interface.

1 Claim, 5 Drawing Sheets

(56)        References Cited

U.S. PATENT DOCUMENTS

| | | | |
|---|---|---|---|
| 2015/0083124 A1* | 3/2015 | Chodkowski ..... | A61M 16/0816 |
| | | | 128/202.27 |
| 2018/0339123 A1 | 11/2018 | Smith | |
| 2020/0289777 A1 | 9/2020 | Bearne | |
| 2021/0077763 A1 | 3/2021 | Huddart | |
| 2021/0077764 A1 | 3/2021 | Peacock | |
| 2022/0126050 A1* | 4/2022 | Freestone ......... | A61M 16/0694 |
| 2022/0395660 A1* | 12/2022 | Scheiner .......... | A61M 16/0605 |

* cited by examiner

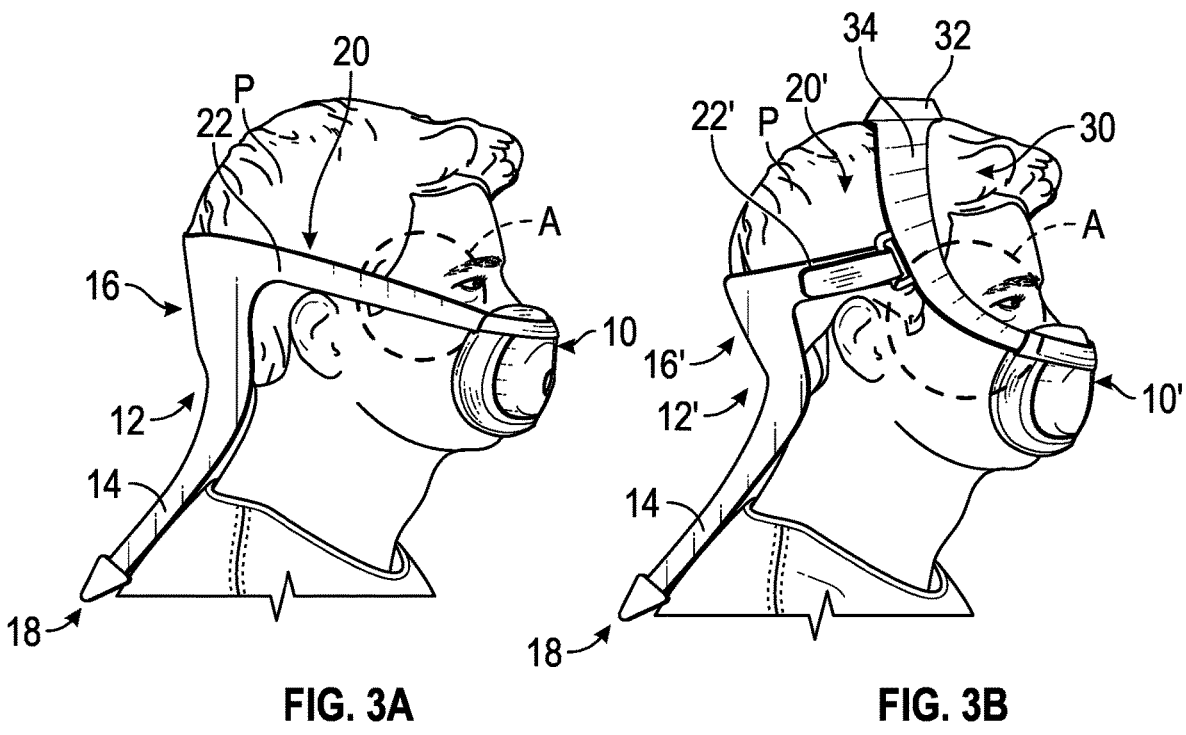
FIG. 3A                FIG. 3B
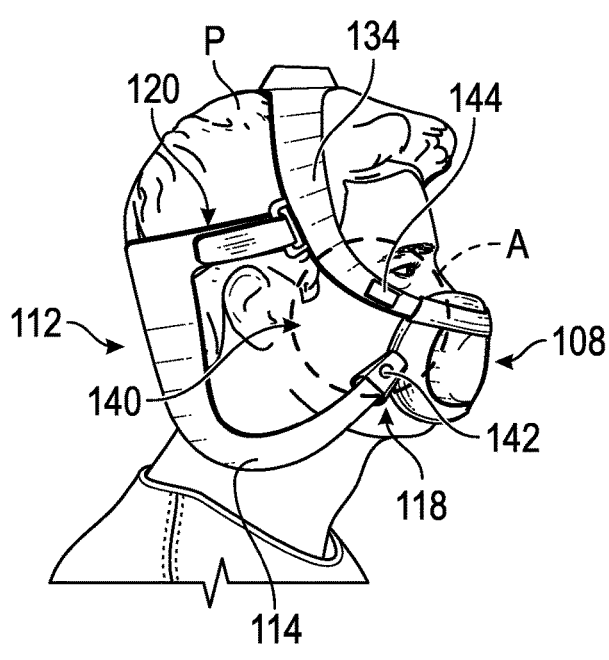
FIG. 4

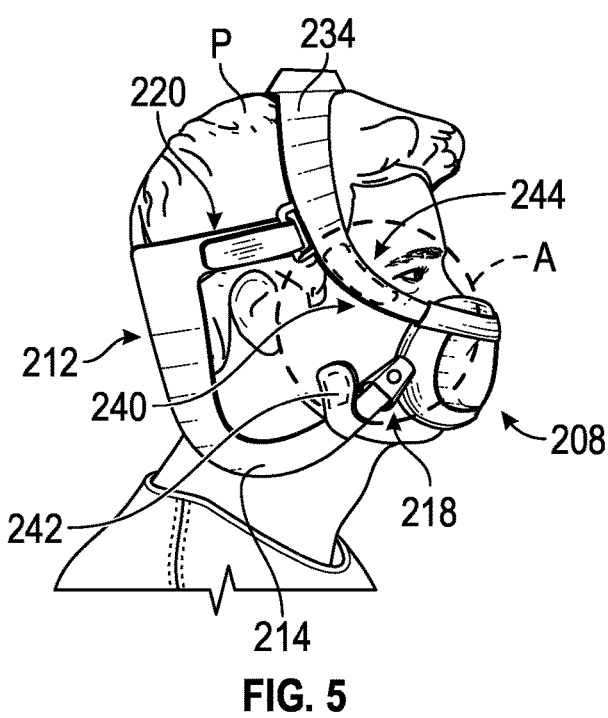
FIG. 5
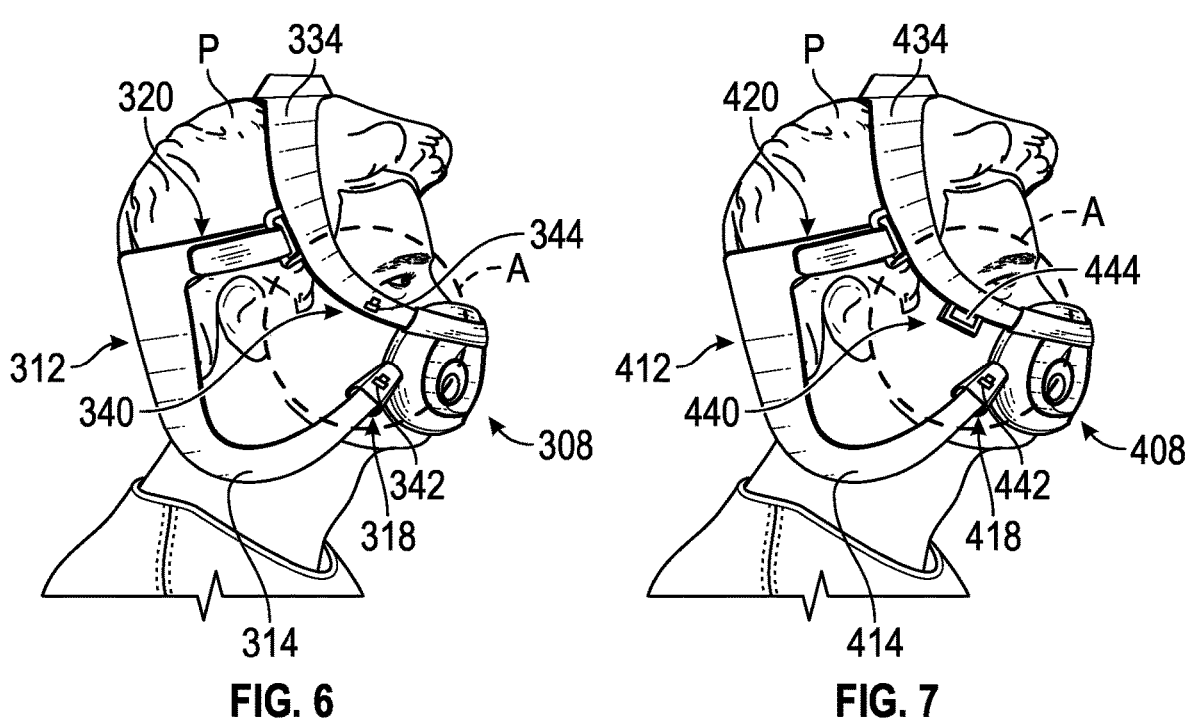
FIG. 6                    FIG. 7

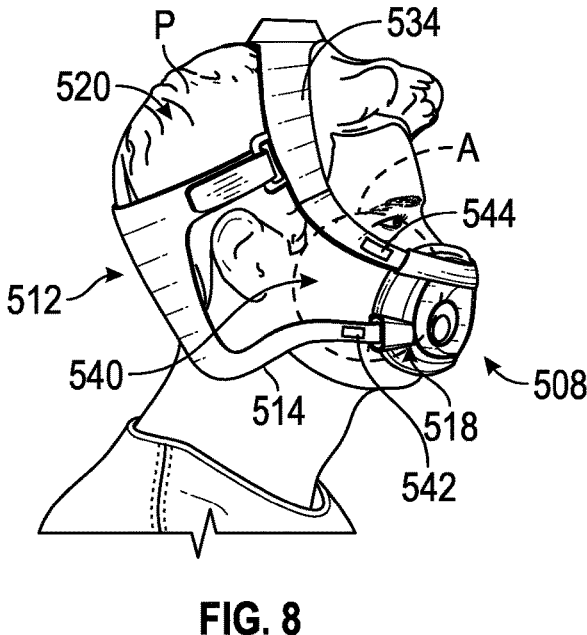
FIG. 8
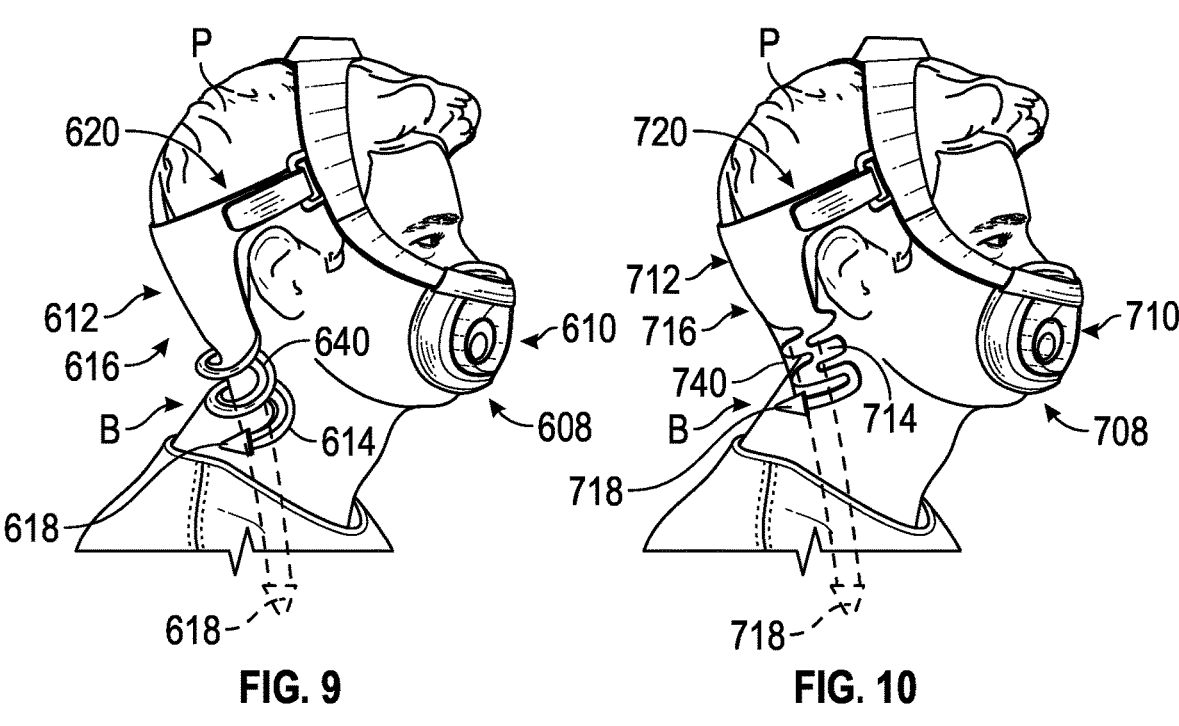
FIG. 9          FIG. 10

ARRANGEMENTS FOR HEADGEAR STRAP MANAGEMENT

CROSS-REFERENCE TO RELATED APPLICATIONS

This patent application claims the priority benefit under 35 U.S.C. § 119(e) of U.S. Provisional Application No. 63/216,825, filed on Jun. 30, 2021, the contents of which are herein incorporated by reference.

BACKGROUND OF THE INVENTION

1. Field of the Invention

The present invention pertains to masks for use in delivering a flow of a breathing gas to an airway of a patient, and, more particularly, to the headgear of such masks that are used to secure the patient interfaces, also of such masks, to the head of a patient. Even more particularly, the present invention pertains to arrangements for use in such headgear that manages/positions one or more ends of the straps of such headgear in a predictable manner.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur when there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface including a mask component having a soft, flexible sealing cushion on the face of the patient. The mask component may be, without limitation, a nasal pillow mask, a nasal mask that covers the patient's nose, a nasal/oral mask that covers the patient's nose and mouth, or a full face mask that covers the patient's face. The patient interface is connected to a gas delivery tube or conduit and interfaces the pressure support device with the airway of the patient, so that a flow of breathing gas can be delivered from the pressure/flow generating device to the airway of the patient via the patient interface. Such patient interfaces may also employ other patient contacting components, such as forehead supports, cheek pads and chin pads.

The patient interface is typically secured to the patient's head by a headgear component, typically referred to simply as headgear. The headgear serves not only to secure the patient interface to the patient's head but also serves to provide stability to the patient interface, as instability of the patient interface can result in leaks and discomfort to the patient. Although the function of headgear in providing stability to the patient interface is vital, the position of headgear by nature lends itself to several usability issues. When removing headgear with more than one strap (e.g., upper strap(s) and lower strap(s)), the lower headgear strap(s) will often fall behind a user's shoulder and back due to the force of gravity. While this movement of the lower strap(s) upon headgear detachment allows for the CPAP system to be easily removed, the specific location of the fallen strap(s) introduces problems for many users, especially those with limited upper body mobility who may not possess the range of motion required to reach free-hanging headgear straps that often fall in the area between a user's shoulder blades. Additionally, the free-hanging location of bottom headgear straps upon detachment from a CPAP mask is often outside of a user's direct field of vision, which can make locating such straps time-consuming and frustrating for the user. Further, the falling movement of two bottom headgear straps following detachment from a CPAP mask in combination with their proximity when unmanaged and free-hanging creates an ideal environment for strap entanglement.

SUMMARY OF THE INVENTION

Embodiments of the present invention improve upon known arrangements and address shortcomings such as previously described by creating a location to which lower headgear straps of a headgear are located upon detachment from the patient interface.

As one aspect of the present invention a headgear arrangement for use in securing a patient interface to the head of a patient is provided. The headgear arrangement comprises: a rear member; a pair of lower strap members, each lower strap member being sized and configured to be positioned on a respective side of the head of the patient when the headgear arrangement is disposed on the head of the patient, each lower strap member extending from a first end that is coupled to, or integrally formed with, the rear member to an opposite, free end that is structured to be selectively directly coupled to the patient interface; an upper portion that extends from the rear member and is structured to be coupled to the patient interface and is sized and configured to generally secure the patient interface to the head of the patient along with the lower strap members when the free ends thereof are directly coupled to the patient interface; and a pair of strap management arrangements, each strap management arrangement positioned on a respective side of the headgear arrangement and structured to locate/hold the free end of a respective one lower strap member of the pair of lower strap members in a predetermined strap management location on the respective side of the head of the patient when the headgear arrangement is positioned on the head of the patient and the free end is not directly coupled to the patient interface.

The strap management location may be forward of an ear of the patient when the headgear arrangement is disposed on the head of the patient.

The strap management location may be on or within an inch of a cheek of the patient when the headgear arrangement is disposed on the head of the patient.

Each strap management arrangement may comprise: a first coupling element positioned at or near the free end of each lower strap member; and a second coupling element provided on the upper portion in the predetermined strap management location, wherein the first coupling element is selectively coupleable to the second coupling element. The first coupling element may be structured to be directly coupled to the patient interface. The first coupling element and the second coupling element may comprise one of: magnetically attractive materials, Velcro segments, cooperating snap and/or frictional fit elements, a clip and corresponding grip element, or one or more adhesive sections.

The strap management location may be below an ear of the patient when the headgear arrangement is disposed on the head of the patient and the head is positioned in an upright position.

The strap management location may be directly beneath the ear of the patient when the headgear arrangement is disposed on the head of the patient and the head is positioned in an upright position.

Each strap management arrangement may comprise a shape retention element provided on, or embedded in, each lower strap member, wherein, when the headgear arrangement is positioned on the head of the patient the shape retention element is movable from: a distorted position in which the free end of the lower strap member is structured to be directly coupled to the patient interface, and a non-distorted, relaxed position in which the free end of the lower strap member is positioned in the strap management location.

The upper portion may comprise a pair of upper strap members.

The upper portion may comprise a tubing assembly that is structured to in-part help secure the patient interface to the head of the patient. The tubing assembly may comprise: a manifold portion that is positioned to be disposed at the top of the head of the patient when the patient interface is secured to the head of the patient by the headgear arrangement, the manifold portion being structured to receive the flow of positive pressure breathing gas from a delivery conduit; a pair of tubular portions, each tubular portion extending from the manifold portion to a distal end that is structured to be coupled to the patient interface; and wherein the upper portion comprises a pair of upper strap members, each upper strap member extending from the rear member to a second end that is coupled to a tubular portion of the pair of tubular portions.

As another aspect of the present invention, a mask for use in providing a regimen of respiratory therapy to a patient is provided. The mask comprises: a patient interface structured to communicate a flow of positive pressure breathing gas to the airway of the patient and a headgear arrangement as previously described.

As yet a further aspect of the present invention, a respiratory interface system adapted to provide a regimen of respiratory therapy to a patient is provided. The respiratory interface system comprises: a pressure generating device structured to generate a flow of a positive pressure breathing gas; a delivery conduit having a first end and an opposite second end, the first end coupled to the pressure generating device; and a mask comprising: a patient interface coupled to the second end of the delivery conduit and structured to communicate the flow of positive pressure breathing gas received from the pressure generating device via the deliver conduit to the airway of the patient; and a headgear arrangement as previously described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 3A and 3B are side elevation views of masks in accordance with example embodiments of the present invention shown positioned on the head of a user with a lower strap of the headgear of the mask uncoupled from the patient interface and a desired strap management location for locating/positioning the free end of the lower strap indicated; and FIGS. 4-10 are side elevation views of masks having strap management arrangements in accordance with some example embodiments of the present invention shown positioned on the head of a patient.

DETAILED DESCRIPTION OF EXEMPLARY EMBODIMENTS

Figure 1A:
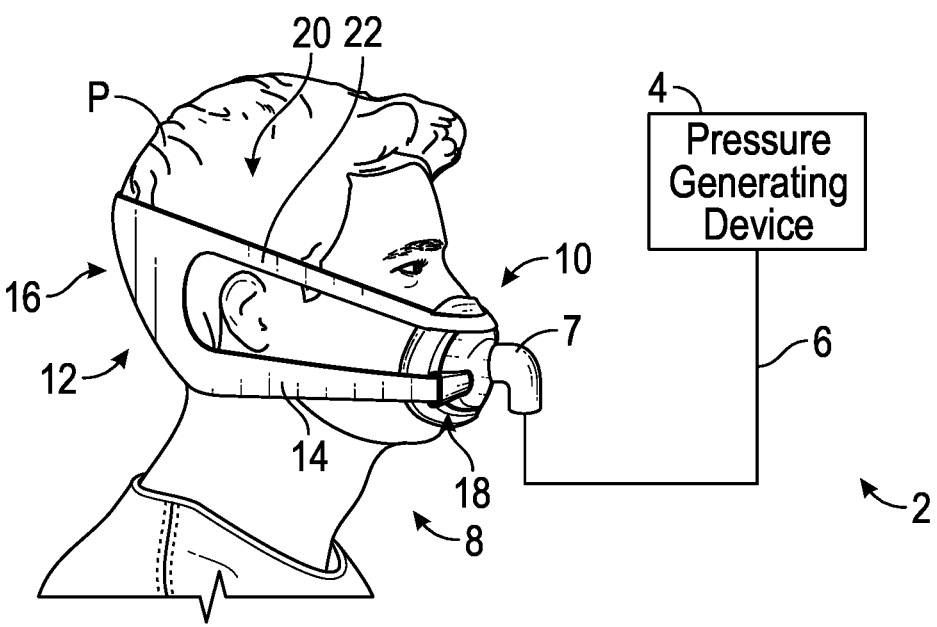
FIG. 1A is a partially schematic depiction of a respiratory interface system adapted to provide a regimen of respiratory therapy to a user/patient shown with a mask thereof, which may be replaced by masks in accordance with example embodiments of the present invention, positioned on the head of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As used herein, the statement that two or more parts or components "engage" one another shall means that the parts exert a force against one another either directly or through one or more intermediate parts or components.

As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

A respiratory interface system 2 adapted to provide a regimen of respiratory therapy to a user/patient P is shown in FIG. 1A. Respiratory interface system 2 includes a pressure generating device 4 (shown schematically) and a delivery conduit 6 (also shown schematically) having a first end coupled to pressure generating device 4 and an opposite second end coupled to a mask 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to mask 8 (e.g., via an elbow 7 or other suitable connector), and mask 8 is structured to further communicate the flow of breathing gas received from conduit 6 to an airway of patient P. Delivery conduit 6 and mask 8 are often collectively referred to as a patient circuit.

Continuing to refer to FIG. 1A, mask 8 is of a conventional design and includes a patient interface 10 and a headgear arrangement 12. Patient interface 10 is structured to engage about the nose and/or mouth of patient P and is coupled to delivery conduit 6 so as to receive the flow of positive pressure breathing gas produced by pressure generating device 4 via delivery conduit 6 and communicate such flow to the airway of patient P. In the example shown in FIG. 1A, patient interface 10 is shown as engaging about both the mouth and nostrils of patient P, however, it is to be appreciated that patient interface 10 may be of any suitable arrangement for providing the flow of positive pressure breathing gas to the nose and/or mouth of patient P without varying from the scope of the present invention.

Figure 1B:
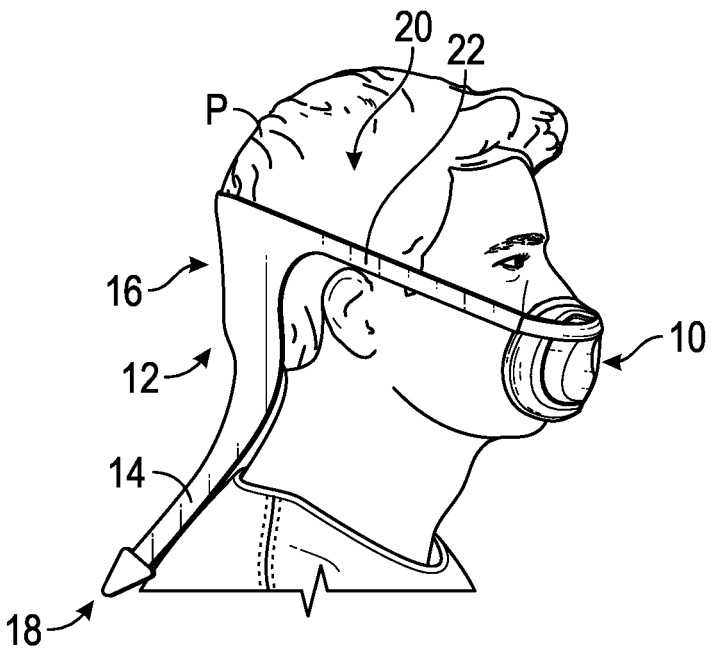
FIG. 1B is a view of the mask of FIG. 1A shown positioned on the head of the patient with a lower strap of the headgear thereof uncoupled from the patient interface thereof and disposed in a typical positioning resulting from the force of gravity.

Referring now to FIG. 1B in addition to FIG. 1A, headgear arrangement 12 is selectively coupled to patient interface 10 so as to selectively secure patient interface 10 to the face/head of patient P. More particularly, headgear arrangement 12 includes a pair of lower strap members 14 (only the lower strap member 14 extending along the right side of the patient P's head of the pair is shown in FIGS. 1A and 1B), with each lower strap member 14 extending from a first end (not numbered) that is coupled to, or integrally formed with, a rear member 16 of headgear arrangement 12 to an opposite, free end 18 that is selectively directly coupled, e.g. via any suitable selective coupling arrangement (e.g., without limitation, snap, Velcro, hook, etc.) to patient interface 10. As used herein, a lower headgear strap is "directly coupled" to a patient interface when such strap is coupled to the patient interface only via the direct engagement of the fastening arrangement of the strap with the corresponding structure of the patient interface. For example, if a snap arrangement between the strap and the interface is utilized to secure the strap to the interface when the strap and interface are directly coupled during a treatment, another coupling that utilizes part of the snap arrangement and another intermediary element to couple the strap and interface is an "indirect" coupling, and not a "direct" coupling.

Continuing to refer to FIGS. 1A and 1B, headgear arrangement 12 further includes an upper portion 20 that may be any suitable arrangement that extends from rear member 16 (and potentially elsewhere) and is coupled (e.g., selectively or otherwise) to patient interface 10 and is sized and configured to generally secure patient interface 8 to the head of patient P along with lower strap members 14 (when the ends 18 thereof are directly coupled to patient interface 10). In the example shown in FIGS. 1A and 1B, upper portion 20 of headgear arrangement 12 includes a pair of upper strap members 22 (only the upper strap member 22 extending along the right side of the patient P's head of the pair is shown in FIGS. 1A and 1B).

Figure 2A:
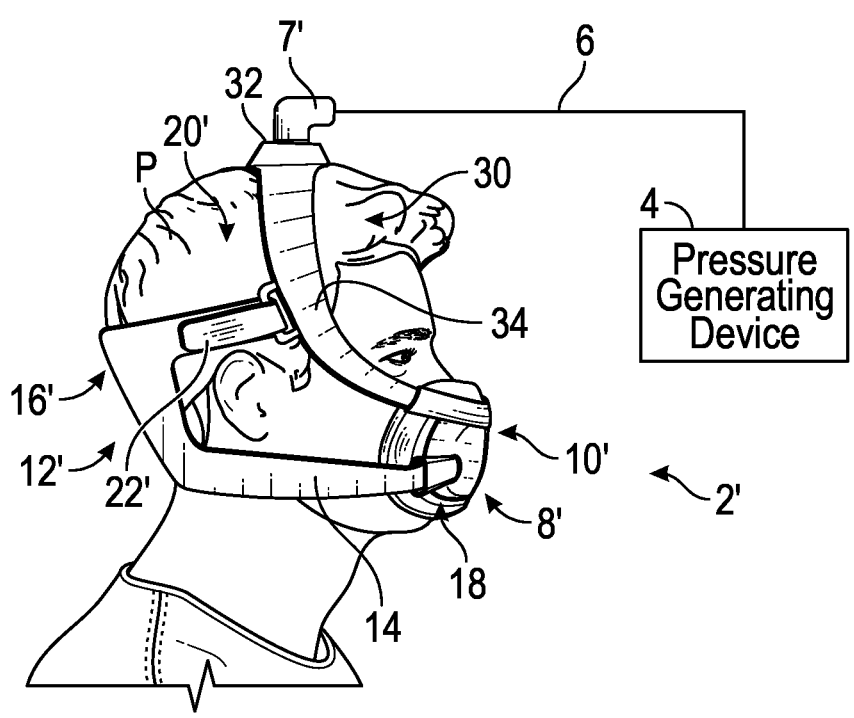
FIG. 2A is a partially schematic depiction of another system for use in providing a flow of positive pressure breathing gas to the airway of a patient shown with a mask thereof, which may also be replaced by masks in accordance with example embodiments of the present invention, shown positioned on the head of a patient.
Figure 2B:
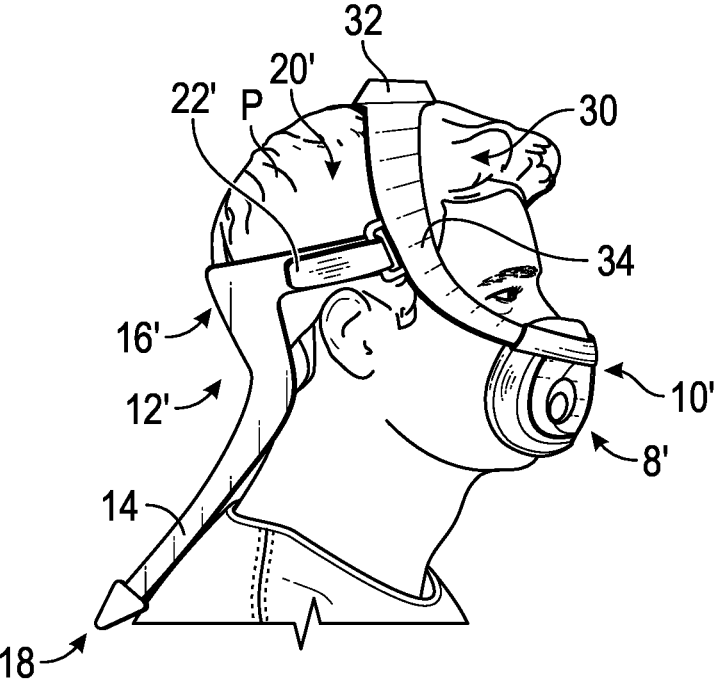
FIG. 2B is a view of the mask of FIG. 2A shown positioned on the head of the patient with a lower strap of the headgear thereof uncoupled from the patient interface thereof and disposed in a typical positioning resulting from the force of gravity.

In another example mask 8' (e.g., without limitation, the Philips DreamWear mask with Full Face Cushion) such as shown in FIGS. 2A and 2B, an upper portion 20' of a headgear arrangement 12' includes a tubing assembly 30 that serves in-part to help secure/stabilize a patient interface 10' to the head of patient P. Tubing assembly 30 includes a manifold portion 32 that is sized and configured to be disposed generally at the top of the patient's head and that is structured to receive the flow of positive pressure breathing gas from delivery conduit 6 (e.g., via an elbow 7' or other suitable connector). Tubing assembly (30) further includes two tubular portions 34 (only one tubular portion 34 extending down along the right side of the head of patient P is shown in FIGS. 2A and 2B) which each extend from manifold portion 32 to a distal end (not numbered) which is selectively coupled to patient interface 10'. In such headgear arrangement 12', upper portion 20' includes a pair of upper straps 22' (only the right side one is shown) that each extend from a rear member 16' to a corresponding tubular portion 34, to which the upper strap 22' is selectable coupled (e.g., via Velcro or other suitable arrangement), as opposed to directly to patient interface 10' such as upper straps 22 of headgear arrangement 12 shown in FIGS. 1A and 1B. Meanwhile, headgear arrangement 12' also includes a pair of lower straps 14 (only the right side is shown) that are positioned and selectively directly coupled to patient interface 10' in a similar manner as lower straps 14 of headgear 12 previously discussed in regard to FIGS. 1A and 1B.

As previously discussed in the Background section, a problem with lower strap members 14 of a headgear arrangement such as either of headgear arrangements 12 or 12' (as well as any other headgear arrangement having similar lower straps) is that upon uncoupling from the associated patient interface, each free end 18 of each lower strap member 14 will often fall behind a user's shoulder and back, such as shown in FIGS. 1B and 2B, due to the force of gravity, which can be problematic for a user in several ways. For example, users with limited upper body mobility may not possess the range of motion required to reach the free-hanging lower headgear straps 14 in such location. Additionally, such location is generally out of the user's field of view, thus adding to the frustration of locating and grasping lower headgear straps 14.

Embodiments of the present invention address such problems caused by uncoupled lower headgear straps 14 by providing strap management arrangements that locate/place free ends 18 of the uncoupled lower headgear straps 14 in known areas that are readily and conveniently accessible to a user. One approach in accordance with example embodiments of the present invention locate/hold free ends 18 of lower headgear straps 14 in strap management locations A (shown as a dashed circle), such as shown in FIGS. 3A and 3B, with a strap management location A located on each side (i.e., the left and right sides) of the patient's head (only location A on the right side of the head of patient P is shown in FIGS. 3A and 3B, it is to be appreciated that the left side that is not shown is generally symmetrical to the right side as shown and thus not described in further details herein).

When located in each location A, free end 18 of each lower headgear strap 14 is readily accessible to patient P for grasping and reattaching to patient interface 10, 10' when adorning mask 8, 8' and securing patient interface 10, 10' thereof to their face for receiving treatment. Strap management locations A are toward the front of the patient's head, forward of each ear of the patient. In some example embodiments of the present invention, each strap management location A is within close proximity to the patient's cheek, preferably on or within one inch thereof. By locating each free end 18 of each lower headgear strap 14 in a defined strap management location A, each free end 18 is much more readily accessible and within a user's field of vision. Hence, the time needed and frustration involved with locating free ends 18 of lower headgear straps 14 for reattachment to patient interface 10, 10' is greatly reduced. Further, the creation of separate strap management locations A for the management of free end 18 of each lower headgear strap 14 eliminates the various problems that users currently face concerning headgear entanglement as the falling movement of two lower headgear straps 14 following detachment from patient interface 10, 10' in combination with their proximity when unmanaged and free-hanging creates an ideal environment for strap entanglement.

For bottom headgear straps 14 that utilize Velcro technology in their adjustability features, the implementation of separate strap management locations reduces the chances for the Velcro systems of the two straps to merge. Keeping the Velcro system of each strap separate ensures the simplest and fastest experience for when a user goes to reattach their headgear to their patient interface. For bottom headgear straps 14 that utilize magnets in their connection to a patient interface, the implementation of separate strap management locations reduces the chances for the two straps' magnetic systems to merge. Preventing this magnetic attraction between both bottom headgear straps 14 allows users to more easily distinguish the left from right straps for eventual reattachment to their patient interface.

Referring now to FIGS. 4-8, masks 108, 208, 308, 408, 508 in accordance with some example embodiments of the present invention are each shown positioned on a head of a patient P. Each of masks 108, 208, 308, 408, 508 are of generally the same arrangement as mask 8' previously discussed in regard to FIGS. 2A and 2B except each of masks 108, 208, 308, 408, 508 further include strap management arrangements 140, 240, 340, 440, 540 provided on each side thereof (only the right side of each mask is shown, it is to be understood that the left side of each mask is generally symmetrical to the right side and thus not separately described in detail herein). Each strap management arrangement 140, 240, 340, 440, 540 utilizes a first coupling element 142, 242, 342, 442, 542 positioned at or near free end 118, 218, 318, 418, 518 of lower headgear strap member 114, 214, 314, 414, 514 that can be selectively coupled to a second coupling element 144, 244, 344, 444, 544 provided on upper portion 120, 220, 320, 420, 520 of each headgear arrangement 112, 212, 312, 412, 512 in order to locate/hold the free end of each lower headgear strap within a strap management location A while each free end is uncoupled from the corresponding patient interface (e.g., when the mask is being taken off or adorned by the patient). Upon the patient putting the mask back on, the free end of each lower headgear strap is then readily accessed in the corresponding strap management location, the first and second coupling elements are readily uncoupled thus releasing the free end of the lower strap from the strap management location A, and the free end is then directly coupled to the patient interface. It is to be appreciated that in each of the example embodiments shown in FIGS. 4-8, the first coupling element 142, 242, 342, 442, 542 may be used as a part of the arrangement(s) used to directly couple the lower headgear strap and the associated free end thereof to the patient interface, or alternatively may be provided as an element in addition to, and separate from, the particular arrangement(s) used in the direct coupling of the free end to the patient interface.

In the examples shown in FIGS. 4-8, second coupling elements 144, 244, 344, 444, 544 are provided on tubular portions 134, 234, 334, 434, 534 of upper portions 120, 220, 320, 420, 520, however, it is to be appreciated that the strap management arrangements 140, 240, 340, 440, 540 described in conjunction with FIGS. 4-8 may likewise be utilized in conjunction with a headgear arrangement 12 such as shown in FIGS. 1A, 1B and 3A or similar thereto with second coupling elements 144, 244, 344, 444, 544 provided on upper strap 22 or other similar structure of upper portion 20 of such alternative headgear instead of on a tubular portion such as shown in FIGS. 4-8.

Although there are many possibilities for creating the aforementioned arrangements of coupling elements, generally they can be organized into two categories: magnetic attachment systems for management and mechanical attachment systems for management. Strap management arrangement 140 shown in FIG. 4 utilizes first and second coupling elements 142 and 144 in the form of magnetic members (shown schematically). First and second magnetic members 142 and 144 may be formed from any suitable magnetic materials (e.g., magnets and/or metallic material(s) attracted to magnets) that are attracted to each other each via magnetic forces. Strap management arrangement 240 shown in FIG. 5 utilizes first and second coupling elements 242 and 244 in the form of cooperating Velcro segments (i.e., a "hooks" section and a "loops" section). Strap management arrangement 340 shown in FIG. 6 utilizes first and second coupling elements 342 and 344 in the form of cooperating snap and/or frictional fit elements (i.e., one or more projecting elements and correspondingly shaped recesses into which the projecting element(s) are held via a snap and/or frictional fit). Strap management arrangement 440 shown in FIG. 7 utilizes a clip mechanism as first coupling element 442 and a corresponding grip as the second coupling element 444 onto which the clip mechanism can be selectively clipped or unclipped. Strap management arrangement 540 shown in FIG. 8 utilizes a number of adhesive sections. Adhesive sections may be used as both of first and second coupling elements 542 and 544, or alternatively a number of adhesive sections may be used for only one of coupling elements 542 or 544, while the other coupling element is an adhesive receiving section structured to have the number of adhesive sections selectively adhered thereto.

FIGS. 9 and 10 show strap management arrangements 640 and 740 in accordance with further example embodiments of the present invention that utilize a slightly different approach to locate/hold free ends 618, 718 of lower headgear straps 614, 714 in other strap management locations B. Similar to strap management locations A, strap management locations B are located on each side of the patient's head (only location B on the right side of the head of patient P is shown in FIGS. 9 and 10, it is to be appreciated that the left side that is not shown is generally symmetrical to the right side as shown and thus not described in further details herein), and when located in each location B, free end 618, 718 of each lower headgear strap 614, 714 is readily accessible to patient P for grasping and reattaching to patient interface 610, 710 when adorning mask 608, 708 and securing patient interface 610, 710 thereof to their face for receiving treatment. Unlike strap management locations A, each strap management location B is toward the rear "corner" of the patient's head, positioned slightly below each ear of the patient and above the shoulder of the patient. In an example embodiment of the present invention, each strap management location B is directly beneath each ear of the patient when the patient's head is positioned in an upright position, such as shown in FIGS. 9 and 10. In another example embodiment of the present invention, each strap management location B is located below and within an inch or less of the ear of the patient. In yet a further example embodiment of the present invention, the strap management location B is located at a midpoint between the ear and shoulder of the patient. By locating each free end 618, 718 of each lower headgear strap 614, 714 in a defined strap management location B, each free end 614, 714 is more readily accessible and generally within a user's field of vision, as opposed to if free ends 618 and 718 were left to fall and freely hang (such as shown in FIGS. 3A and 3B and/or in hidden line in FIGS. 9 and 10). Hence, the time needed and frustration involved with locating free ends 618, 718 of lower headgear straps 614, 714 for reattachment to patient interface 610, 710 is greatly reduced. Further, the creation of separate areas B for the management of free end 618, 718 of each lower headgear strap 614, 714 eliminates the various problems that patients currently face concerning headgear entanglement such as previously discussed herein.

Continuing to refer to FIGS. 9 and 10, each strap management arrangement 640, 740 is structured to automatically locate the associated free end 618, 718 in a corresponding strap management location B upon uncoupling of free end 618, 718 from the corresponding patient interface 610, 710 (and release of the lower strap/free end from any grasp by the patient). In the example embodiment shown in FIG. 9, strap management arrangement 640 is in the form of a shape retention element coupled to, or embedded in, lower headgear strap 614. The shape retention element may be formed from a plastic, metal, or other suitable material or materials that is/are distortable from a default positioning, in which the retention element, and thus lower headgear strap 614, is generally coiled in a spring-like or similar bunched manner (e.g., such as shown in FIG. 9), to a generally straight, elongated position such that lower headgear strap 614 can be positioned similar to strap 14 of FIG. 2A with free end 618 coupled to patient interface 610. Upon uncoupling of free end 618 from patient interface 610, shape retention element returns to its default positioning, thus effectively coiling/bunching lower headgear strap 614 in a manner such that free end 618 thereof automatically moves to strap management location B, such as shown in FIG. 9.

In the example embodiment shown in FIG. 10, strap management arrangement 740 is in the form of an elastic member coupled to, or embedded in, lower headgear strap 714. The elastic member may be formed from rubber, spandex, lycra, or other suitable material or materials that may be stretched from a default length, in which the elastic element is its shortest, and thus lower headgear strap 714 is generally bunched in a pleated or similar manner (e.g., such as shown in FIG. 10), to a stretched position such that lower headgear strap 714 can be positioned similar to lower headgear strap 14 of FIG. 2A with free end 718 coupled to patient interface 710. Upon uncoupling of free end 718 from patient interface 710, the elastic member returns to its default length, thus effectively bunching lower headgear strap 714 resulting in free end 718 thereof automatically moving to strap management location B, such as shown in FIG. 10.

From the foregoing it is thus to be appreciated that embodiments of the present invention provide strap management arrangements that improve the usability of headgear arrangements and patient interfaces associated therewith used in respiratory interface systems for providing a regimen of respiratory therapy to a user/patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A mask for use in providing a regimen of respiratory therapy to a patient, the mask comprising:

(a) a patient interface structured to communicate a flow of positive pressure breathing gas to the airway of the patient, the patient interface comprising;
  (1) a cushion adapted to seal against a surface of the patient,
  (2) a frame coupled to the cushion, and (b) a headgear arrangement for securing the patient interface to the head of the patient, the headgear arrangement comprising:
  (1) a rear member;
  (2) a pair of lower strap members, each lower strap member being sized and configured to be positioned on a respective side of the head of the patient when the headgear arrangement is disposed on the head of the patient, each lower strap member extending from a first end that is coupled to, or integrally formed with, the rear member to an opposite, free end that is selectively directly coupled to the patient interface;
  (3) a tubular upper portion that extends from the rear member and is coupled to the patient interface and is sized and configured to generally secure the patient interface to the head of the patient along with the lower strap members when the free ends thereof are directly coupled to the patient interface, wherein the tubular upper straps are hollow and define a gas carrying conduit to deliver gas to patient interface; and
  (4) a pair of strap management arrangements, each strap management arrangement positioned on a respective side of the headgear arrangement and structured to locate/hold the free end of a respective one lower strap member of the pair of lower strap members in a predetermined strap management location on the respective side of the head of the patient when the headgear arrangement is positioned on the head of the patient and the free end is not directly coupled to the patient interface, wherein each strap management arrangement comprises:
    (i) a first coupling element positioned at the free end of each lower strap member; and
    (ii) a second coupling element provided on the upper portion in the predetermined strap management location, wherein the first coupling element is selectively coupleable to the second coupling element, and wherein the first coupling element and the second coupling element comprise one of: magnetically attractive materials, hook-and-loop segments, cooperating snap and/or frictional fit elements, a clip and corresponding grip element, or one or more adhesive sections; wherein the first coupling element is not able to be coupled to the tubular upper portion when selectively coupled to the patient interface.

* * * * *